(12) United States Patent  
Crothers et al.

(10) Patent No.: US 9,336,588 B2
(45) Date of Patent: May 10, 2016

(54) JOINT ASSEMBLIES AND METHOD OF INSPECTING THEREOF

(71) Applicant: The Boeing Company, Huntington Beach, CA (US)

(72) Inventors: Phillip Crothers, Hampton East (AU); Leo Christodoulou, Arlington, VA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/504,015

(22) Filed: Oct. 1, 2014

(65) Prior Publication Data

US 2016/0098826 A1    Apr. 7, 2016

(51) Int. Cl.
  *G06K 9/00* (2006.01)
  *G06T 7/00* (2006.01)

(52) U.S. Cl.
  CPC ..... *G06T 7/0004* (2013.01); *G06T 2207/10004* (2013.01); *G06T 2207/30164* (2013.01)

(58) Field of Classification Search
  USPC ................. 382/141, 149, 152; 156/60, 64, 66
  See application file for complete search history.

(56) References Cited

U.S. PATENT DOCUMENTS

| | | | |
|---|---|---|---|
| 4,090,899 A | | 5/1978 | Reich |
| 4,689,104 A * | | 8/1987 | Lavendel ............. B23K 35/004 156/150 |
| 4,955,740 A | | 9/1990 | Renz et al. |
| 5,812,925 A | | 9/1998 | Ecer |
| 5,833,795 A * | | 11/1998 | Smith .................... B29C 73/02 156/272.4 |
| 5,841,034 A * | | 11/1998 | Ball .................... G01M 11/086 73/800 |
| 7,422,141 B2 * | | 9/2008 | Pikulski ............. B23K 35/0244 228/245 |
| 7,617,695 B2 * | | 11/2009 | Shapiro ................. F25B 49/022 62/175 |
| 8,641,845 B2 | | 2/2014 | Bruck |
| 8,661,669 B2 * | | 3/2014 | Andrews ............ B23K 15/0093 29/525.14 |

FOREIGN PATENT DOCUMENTS

EP    2192602 A1    6/2010

OTHER PUBLICATIONS

Extended European Search Report for related application 15178866.8 dated Feb. 24, 2016; 8 pp.

* cited by examiner

*Primary Examiner* — Yosef Kassa
(74) *Attorney, Agent, or Firm* — Armstrong Teasdale LLP

(57) ABSTRACT

A joint assembly is provided. The joint assembly includes a first component including a first bond surface and a second component including a second bond surface coupled to the first bond surface such that a bond line is defined therebetween. At least one of the first and second components includes a plurality of contrast particles that diffuse across the bond line when a predetermined amount of heat and pressure are applied to the first and second components.

20 Claims, 3 Drawing Sheets

JOINT ASSEMBLIES AND METHOD OF INSPECTING THEREOF

BACKGROUND

The field of the present disclosure relates generally to composite joints and, more specifically, to non-destructive bond strength verification techniques for composite joints.

At least some known aircraft components may be fabricated from multi-layer laminate structures of non-metallic composite materials such as carbon-fiber-reinforced polymer (CFRP). Composite materials generally have a high strength-to-weight ratio and may be formed in a variety of shapes and sizes. To reduce the weight of an aircraft, the composite materials may be used in combination with metallic materials, such as aluminum, titanium, and/or steel. Reducing overall weight generally contributes to increasing the fuel efficiency of the aircraft.

At least some known aircraft components fabricated from composite materials may be bonded together with an adhesive material. While the adhesive material is generally effective at bonding the components together, disbonding may occur during the service life of the aircraft. For example, disbonding may occur after prolonged use of the aircraft and/or may be caused when a foreign object impacts the materials during flight. Such disbonding may be difficult to detect during scheduled maintenance, and may be difficult to detect via visual inspection.

Moreover, it may be difficult and costly to verify that a successful bond between the components has been formed during manufacture of a part. For example, at least one known method of verifying bond strength includes forming process verification coupons using the same process under the same conditions as the part being formed. The strength of the process verification coupons is then evaluated via destructive testing, and the part is certified for service if the bond strength of the coupons is greater than a predetermined threshold. However, forming and evaluating process verification coupons is a time-consuming and laborious task, which provides only indirect bond strength verification of the bond formed between the components.

BRIEF DESCRIPTION

In one aspect, a joint assembly is provided. The joint assembly includes a first component including a first bond surface and a second component including a second bond surface coupled to the first bond surface such that a bond line is defined therebetween. At least one of the first and second components includes a plurality of contrast particles that diffuse across the bond line when a predetermined amount of heat and pressure are applied to the first and second components.

In another aspect, a joint assembly is provided. The joint assembly includes a first component including a first bond surface and a second component including a second bond surface configured to couple to said first bond surface. The joint assembly also includes a layer of adhesive positioned between the first and second bond surfaces such that a first bond line is defined between the layer and the first bond surface, and such that a second bond line is defined between the layer and the second bond surface. The layer of adhesive includes a plurality of contrast particles that diffuse across at least one of the first and second bond lines when a predetermined amount of heat and pressure are applied to the first and second components.

In yet another aspect, a method of inspecting a joint assembly is provided. The method includes evaluating the joint assembly via a non-destructive inspection technique, obtaining an image of the joint assembly, and verifying bond formation between components in the joint assembly based on a location of contrast particles in the image. The contrast particles diffuse from a first location into at least one of the components when a predetermined amount of heat and pressure are applied to the components.

DETAILED DESCRIPTION

The implementations described herein relate to joint assemblies and methods of inspecting thereof. More specifically, the methods described herein enable direct verification of bond formation between components in the joint assemblies, wherein the bond is formed in thermoplastic materials via diffusion at a bond interface. The direct verification is provided by evaluating the joint assemblies via non-destructive inspection (NDI) techniques, and the joint assemblies include contrast particles dispersed therein that are capable of detection when evaluated by the NDI techniques. For example, the contrast particles are initially either located in the components themselves or in a layer of adhesive positioned between the components. When a predetermined amount of heat and pressure are applied, such as an amount of heat and pressure traditionally used to form the joint assemblies, the contrast particles diffuse across a bond line defined between the components. A location of the contrast particles in the finished joint assembly is determined by the NDI evaluation, and successful bond verification is confirmed when the contrast particles are located within adjacent components of the assembly (i.e., when diffusion occurs).

Figure 1:
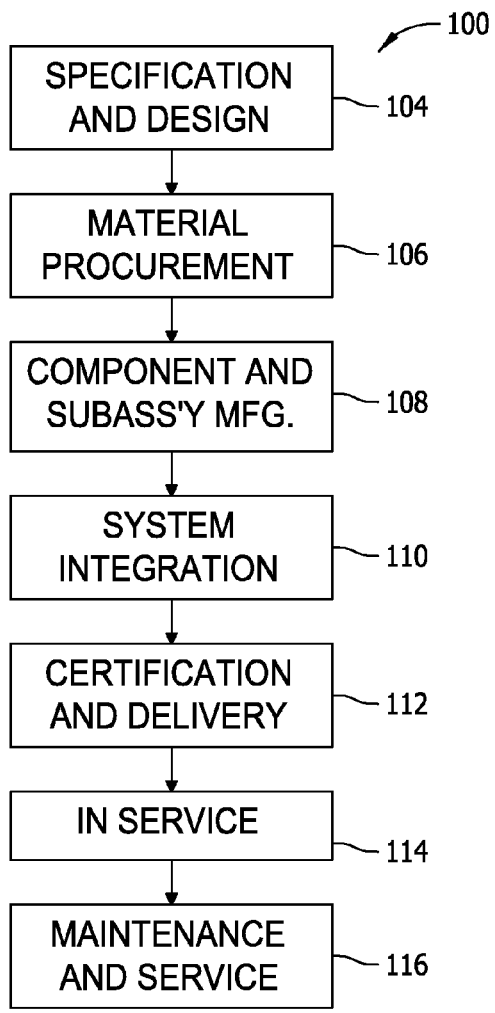
FIG. 1 is a flow diagram of an exemplary aircraft production and service method.
Figure 2:
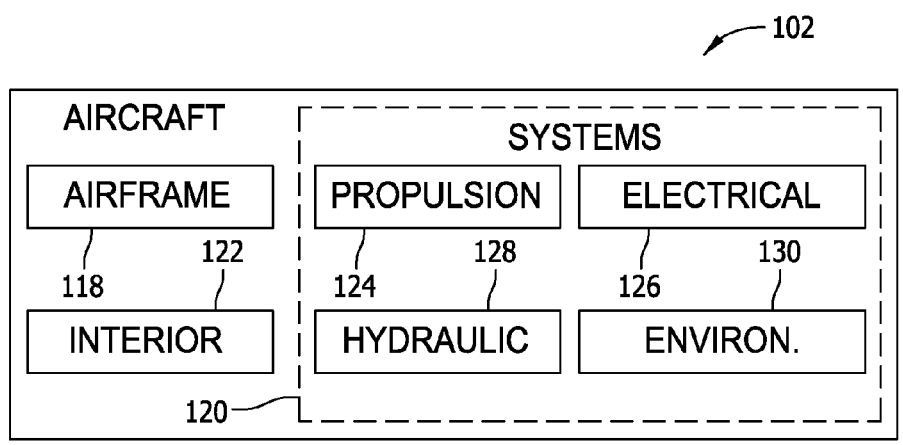
FIG. 2 is a block diagram of an exemplary aircraft.

Referring to the drawings, implementations of the disclosure may be described in the context of an aircraft manufacturing and service method 100 (shown in FIG. 1) and via an aircraft 102 (shown in FIG. 2). During pre-production, including specification and design 104 data of aircraft 102 may be used during the manufacturing process and other materials associated with the airframe may be procured 106. During production, component and subassembly manufacturing 108 and system integration 110 of aircraft 102 occurs, prior to aircraft 102 entering its certification and delivery process 112. Upon successful satisfaction and completion of airframe certification, aircraft 102 may be placed in service 114. While in service by a customer, aircraft 102 is scheduled for periodic, routine, and scheduled maintenance and service 116, including any modification, reconfiguration, and/or refurbishment, for example. In alternative implementations, manufacturing and service method 100 may be implemented via platforms other than an aircraft.

Each portion and process associated with aircraft manufacturing and/or service 100 may be performed or completed by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 2, aircraft 102 produced via method 100 may include an airframe 118 having a plurality of systems 120 and an interior 122. Examples of high-level systems 120 include one or more of a propulsion system 124, an electrical system 126, a hydraulic system 128, and/or an environmental system 130. Any number of other systems may be included.

Apparatus and methods embodied herein may be employed during any one or more of the stages of method 100. For example, components or subassemblies corresponding to component and subassembly production process 108 may be fabricated or manufactured in a manner similar to components or subassemblies produced while aircraft 102 is in service 114. Also, one or more apparatus implementations, method implementations, or a combination thereof may be utilized during the production stages 108 and 110, for example, by substantially expediting assembly of, and/or reducing the cost of assembly of aircraft 102. Similarly, one or more of apparatus implementations, method implementations, or a combination thereof may be utilized while aircraft 102 is being serviced or maintained, for example, during scheduled maintenance and service 116.

As used herein, the term "aircraft" may include, but is not limited to only including, airplanes, unmanned aerial vehicles (UAVs), gliders, helicopters, and/or any other object that travels through airspace. Further, in an alternative implementation, the aircraft manufacturing and service method described herein may be used in any manufacturing and/or service operation.

Figure 3:
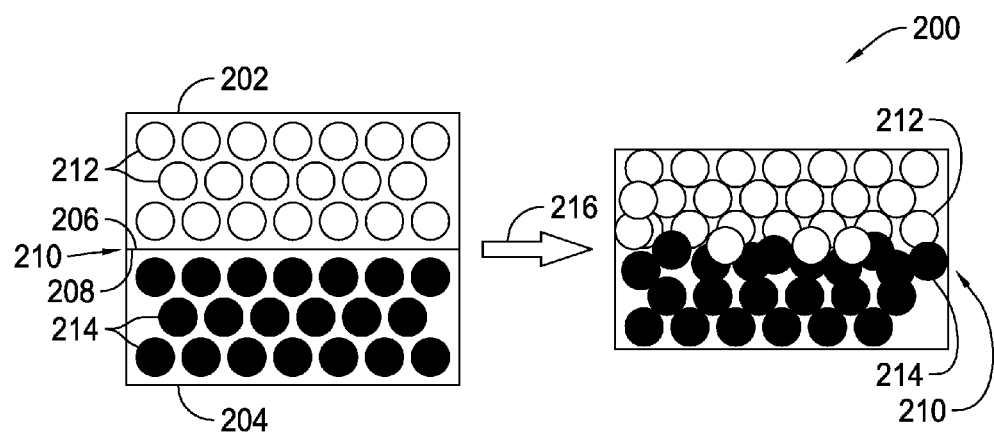
FIG. 3 is a schematic flow diagram illustrating a series of process steps of forming an exemplary joint assembly.

FIG. 3 is a schematic flow diagram illustrating a series of process steps of forming an exemplary joint assembly 200. In the exemplary implementation, joint assembly 200 includes a first component 202 and a second component 204. First component 202 includes a first bond surface 206 and second component 204 includes a second bond surface 208 coupled to first bond surface 206 such that a bond line 210 is defined therebetween. Moreover, at least one of first and second components 202 and 204 include a plurality of contrast particles dispersed therein. Specifically, in one implementation, first component 202 includes a plurality of first contrast particles 212 dispersed therein, and second component 204 includes a plurality of second contrast particles 214 dispersed therein. As will be described in more detail below, contrast particles 212 and 214 diffuse across bond line 210 when a predetermined amount of heat and pressure 216 are applied to first and second components 202 and 204.

First and second components 202 and 204 may be fabricated from any material that enables joint assembly 200 to function as described herein. An exemplary material used to fabricate components 202 and 204 includes thermoplastic material such as, but not limited to, carbon fiber reinforced polymer. As such, fabricating components 202 and 204 from thermoplastic material enables contrast particles 212 and 214 to be dispersed therein during formation thereof.

First and second contrast particles 212 and 214 may be fabricated from any material that enables joint assembly 200 to function as described herein. Specifically, in one implementation, first contrast particles 212 are fabricated from a first material and second contrast particles 214 are fabricated from a second material different than the first material in at least one feature such as material or size, for example. The materials used to fabricate first and second contrast particles 212 and 214 are selected based on whether the materials are capable of detection when joint assembly 200 is evaluated by non-destructive inspection techniques. For example, if the non-destructive inspection technique implemented is eddy current testing, contrast particles 212 and 214 are fabricated from an electrically conductive material such as graphene.

Moreover, as described above, the first and second materials differ in at least one feature such that differentiation between first and second contrast particles 212 and 214 can be determined when evaluated by non-destructive inspection techniques. As such, as will be described in more detail below, bond formation between first and second components 202 and 204 can be verified based on a location of contrast particles 212 and 214 in joint assembly 200. In an alternative implementation, only one of first and second components 202 and 204 includes contrast particles such that bond formation is detected when the contrast particles diffuse across bond line 210.

First and second contrast particles 212 and 214 may also be of any size that enables joint assembly 200 to function as described herein. For example, in the exemplary implementation, contrast particles 212 and 214 have a size of less than about 100 nanometers such that contrast particles 212 and 214 readily diffuse across bond line 210 when heat and pressure 216 are applied. Moreover, utilizing particles of this size facilitates reducing modifications to the mechanical properties of the material used to fabricate first and second components 202 and 204.

In the series of process steps, first and second bond surfaces 206 and 208 are coupled together and heat and pressure 216 are applied to first and second components 202 and 204 forming a substantially unitary structure. Heat and pressure 216 facilitates softening the thermoplastic material of components 202 and 204 such that at least some of contrast particles 212 and 214 diffuse across bond line 210. As such, bond formation between components 202 and 204 can be verified based on a location of contrast particles 212 and 214 in joint assembly 200. More specifically, bond formation is verified based on a concentration of contrast particles 212 and 214 within a predetermined volume at a location within joint assembly 200, or a distance that either contrast particles 212 and 214 diffuse into opposing components 202 and 204, respectively.

Figure 4:
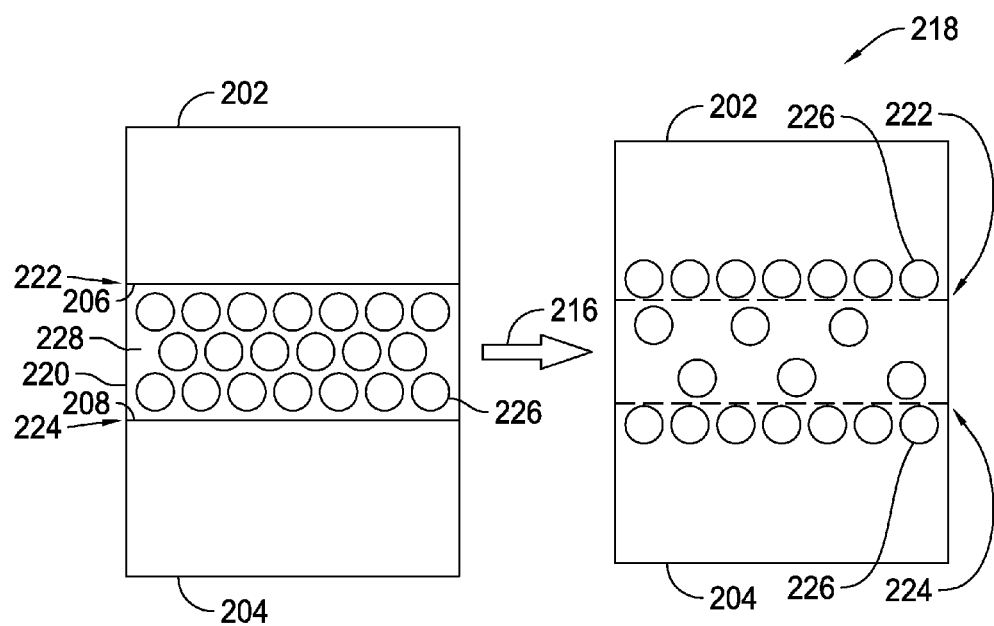
FIG. 4 is a schematic flow diagram illustrating a series of process steps of forming an alternative joint assembly.

FIG. 4 is a schematic flow diagram illustrating a series of process steps of forming an alternative joint assembly 218. In the exemplary implementation, joint assembly 218 includes first component 202 and second component 204, and bond surfaces 206 and 208 are coupled indirectly together. A layer 220 of adhesive is positioned between bond surfaces 206 and 208 such that a first bond line 222 is defined between layer 220 and first bond surface 206, and a second bond line 224 is defined between layer 220 and second bond surface 208. Moreover, unlike joint assembly 200 (shown in FIG. 3), first and second components 202 and 204 do not include contrast particles 212 and 214 dispersed therein. Rather, as will be described in more detail below, layer 220 of adhesive includes a plurality of contrast particles 226 that diffuse across at least one first and second bond lines 222 and 224 when a predetermined amount of heat and pressure 216 are applied to first and second components 202 and 204.

Layer 220 of adhesive includes a resin matrix 228 and contrast particles 226 dispersed therein. Resin matrix 228 may be any material that enables joint assembly 218 to function as described herein. In the exemplary implementation, resin matrix 228 is fabricated from a third material that differs from the first material used to fabricate contrast particles 226 such that differentiation therebetween can be determined when evaluated by non-destructive inspection techniques.

In the series of process steps, layer 220 of adhesive is positioned between first and second components 202 and 204 and heat and pressure 216 are applied thereto. Heat and pressure 216 facilitates softening the thermoplastic material of components 202 and 204, and facilitates curing layer 220 of adhesive. As layer 220 cures, contrast particles 226 dispersed therein diffuse across at least one of first and second bond lines 222 and 224. As such, bond formation between components 202 and 204 can be verified based on a location of contrast particles 226 in joint assembly 218. More specifically, bond formation is verified based on a distance that contrast particles 226 diffuse into each of components 202 and 204.

Figure 5:
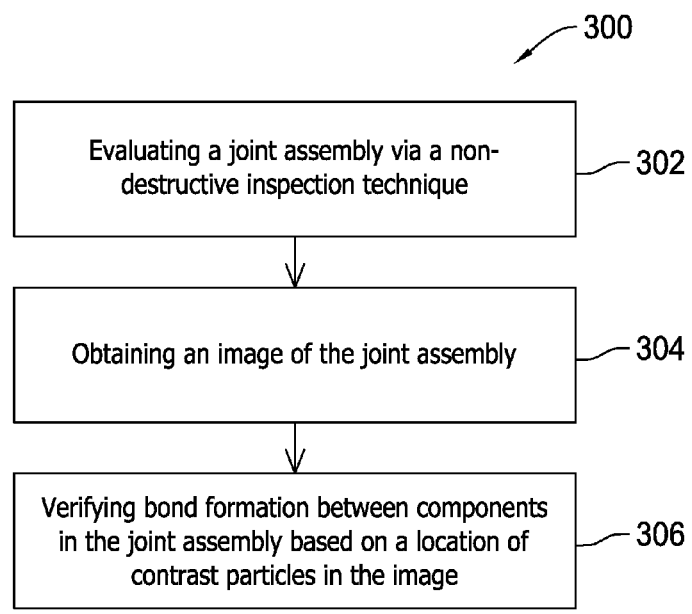
FIG. 5 is a flow diagram of an exemplary method of inspecting a joint assembly.

FIG. 5 is a flow diagram of an exemplary method 300 of inspecting a joint assembly, such as joint assemblies 200 or 218 (shown in FIGS. 3 and 4). In the exemplary implementation, method 300 includes evaluating 302 the joint assembly via a non-destructive inspection technique, and obtaining 304 an image of the joint assembly. Exemplary non-destructive inspection techniques include, but are not limited to, eddy current testing, tomography, terahertz imaging techniques, or x-ray imaging techniques. In one implementation, the joint assembly is evaluated 302 along a bond line, such as bond lines 210, 222, or 224, defined between components of the joint assembly.

Method 300 also includes verifying 306 bond formation between components in the joint assembly based on a location of contrast particles in the image. The contrast particles diffuse from a first location into at least one of the components when a predetermined amount of heat and pressure are applied to the components. For example, the first location is within one of components 202 and 204 when evaluating joint assembly 200, and the first location is within layer 220 of adhesive when evaluating joint assembly 218. In one implementation, a resolution of the image is verified to be greater than a predetermined image quality threshold prior to verifying bond formation between components in the joint assembly. If the resolution is less than the predetermined image quality threshold, subsequent images are obtained until a suitable image has been obtained.

As described above, verifying 306 bond formation includes determining at least one of a concentration of the contrast particles at the location of the joint assembly or a distance that the contrast particles diffuse into the at least one of the components. Moreover, verifying 306 bond formation includes determining differentiation between a first material used to fabricate the plurality of contrast particles and a second material used to fabricate the components, or between first and second materials if both are used to fabricate the components.

This written description uses examples to disclose various implementations, including the best mode, and also to enable any person skilled in the art to practice the various implementations, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A joint assembly comprising:
   a first component comprising a first bond surface; and
   a second component comprising a second bond surface coupled to said first bond surface such that a bond line is defined therebetween,
   wherein at least one of said first and second components comprises a plurality of contrast particles that diffuse across said bond line when a predetermined amount of heat and pressure are applied to said first and second components.

2. The assembly in accordance with claim 1, wherein said first component comprises a plurality of first contrast particles fabricated from a first material and said second component comprises a plurality of second contrast particles fabricated from a second material different than the first material.

3. The assembly in accordance with claim 2, wherein said pluralities of first and second contrast particles are interspersed with each other when the predetermined amount of heat and pressure are applied.

4. The assembly in accordance with claim 1, wherein said plurality of contrast particles are fabricated from a first material capable of detection when evaluated by non-destructive inspection techniques.

5. The assembly in accordance with claim 4, wherein said plurality of contrast particles are fabricated from the first material different than a second material used to fabricate said first and second components such that differentiation between the first and second materials is determined when evaluated by the non-destructive inspection techniques.

6. The assembly in accordance with claim 1, wherein said first and second components are fabricated from a thermoplastic material.

7. The assembly in accordance with claim 1, wherein contrast particles of said plurality of contrast particles have a size of less than about 100 nanometers.

8. A joint assembly comprising:
   a first component comprising a first bond surface;
   a second component comprising a second bond surface configured to couple to said first bond surface; and
   a layer of adhesive positioned between said first and second bond surfaces such that a first bond line is defined between said layer and said first bond surface, and such that a second bond line is defined between said layer and said second bond surface, wherein said layer of adhesive comprises a plurality of contrast particles that diffuse across at least one of said first and second bond lines when a predetermined amount of heat and pressure are applied to said first and second components.

9. The assembly in accordance with claim 8, wherein said layer of adhesive comprises a resin matrix and said plurality of contrast particles dispersed within said resin matrix.

10. The assembly in accordance with claim 8, wherein said plurality of contrast particles are fabricated from a material capable of detection when evaluated by non-destructive inspection techniques.

11. The assembly in accordance with claim 10, wherein said plurality of contrast particles are fabricated from the first material different than a second material used to fabricate said first and second components such that differentiation between the first and second materials is detected when evaluated by the non-destructive inspection techniques.

12. The assembly in accordance with claim 10, wherein said plurality of contrast particles are fabricated from the first material different than a third material used to fabricate said resin matrix.

13. The assembly in accordance with claim 8, wherein said first and second components are fabricated from a thermoplastic material.

14. The assembly in accordance with claim 8, wherein contrast particles of said plurality of contrast particles have a size of less than about 100 nanometers.

15. A method of inspecting a joint assembly, said method comprising:
    evaluating the joint assembly via a non-destructive inspection technique;
    obtaining an image of the joint assembly; and
    verifying bond formation between components in the joint assembly based on a location of contrast particles in the image, wherein the contrast particles diffuse from a first location into at least one of the components when a predetermined amount of heat and pressure are applied to the components.

16. The method in accordance with claim 15 further comprising verifying a resolution of the image is greater than a predetermined image quality threshold.

17. The method in accordance with claim 15, wherein verifying bond formation comprises determining at least one of a concentration of the contrast particles at the location within the joint assembly or a distance that the contrast particles diffuse into the at least one of the components.

18. The method in accordance with claim 15, wherein verifying bond formation comprises determining differentiation between a first material used to fabricate the plurality of contrast particles and a second material used to fabricate the components.

19. The method in accordance with claim 15, wherein evaluating the joint assembly comprises evaluating the joint assembly along a bond line defined between the components.

20. The method in accordance with claim 19 further comprising certifying the joint assembly for service when the contrast particles diffuse across the bond line.

\* \* \* \* \*